United States Patent [19]

Lukenbach et al.

[11] Patent Number: 4,617,414

[45] Date of Patent: Oct. 14, 1986

[54] PROCESS FOR THE PREPARATION OF PHOSPHATE SURFACTANTS

[75] Inventors: Elvin R. Lukenbach, Somerset; Richard R. Tenore, Martinsville, both of N.J.

[73] Assignee: Johnson & Johnson Baby Products Company, New Brunswick, N.J.

[21] Appl. No.: 649,031

[22] Filed: Sep. 10, 1984

[51] Int. Cl.$^4$ .............................. C07F 9/08; C11C 3/00
[52] U.S. Cl. ...................................... 558/87; 260/403; 544/57; 544/151; 544/337
[58] Field of Search .......................... 558/87; 260/403; 544/57, 151, 337

[56] References Cited

U.S. PATENT DOCUMENTS 4,215,064  7/1980  Lindemann et al. ................ 260/403
4,261,911  4/1981  Lindemann et al. ................ 260/403
4,382,036  5/1983  Lindemann et al. ................ 260/403

*Primary Examiner*—Anton H. Sutto
*Attorney, Agent, or Firm*—Steven P. Berman

[57] ABSTRACT

A process for the preparation of phosphate compounds comprising (1) reacting an inorganic phosphate salt with epihalohydrin to obtain a phosphate ester and (2) reacting the phosphate ester with a substituted amine wherein step (1) is carried out at a pH of from about 5.4 to 7.0.

4 Claims, No Drawings

PROCESS FOR THE PREPARATION OF PHOSPHATE SURFACTANTS

BACKGROUND OF THE INVENTION

The present invention relates to a process for the preparation of phosphate surfactants. More particularly, the invention relates to an improved process for the preparation of surfactants containing a hydroxypropylene phosphate group.

The phosphate substituted surfactants include phosphobetaines of the formula

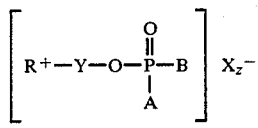

wherein
A is selected from $O^-$, OM and $-O-Y-R^+$
B is selected from $O^-$ and OM
$X^-$ is an anion
Z is an integer from 0 to 2 with the proviso that only one of A and B can be $O^-$ and Z is of a value necessary for charge balance,
R is an amine or an amidoamine reactant moiety, and
Y is alkylene or substituted alkylene.

These phosphobetaine surfactants are fully described in U.S. Pat. No. 4,215,064 which is incorporated herein by reference.

The phosphate substituted surfactants also include phosphitaines of the formula

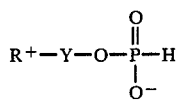

wherein R is an amine or an amidoamine reactant moiety and Y is alkylene or substituted alkylene. These phosphitaine compounds are more fully described in U.S. Pat. No. 4,261,911 which is incorporated herein by reference.

The phosphate substituted surfactants may also include pyrophosphobetaines of the formula

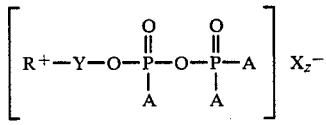

wherein
A is selected from $O^-$, OM and $O-Y-R^+$ with the proviso that at least one A is $O^-$
X is an anion
Z is an integer from 0 to 3, a value necessary for charge balance,
R is an amine or amidoamine moiety, and
Y is alkylene or substituted alkylene.

These pyrophosphobetaine compounds are more fully described in U.S. Pat. No. 4,382,036, which is incorporated herein by reference.

The phosphate substituted surfactants described above all exhibit outstanding foaming, viscosity-building, wetting, cleansing, detergency, anti-static and emulsifying properties and are, therefore, useful in industrial applications calling for high performance surface active agents. The compounds are also highly stable species and are extremely well tolerated by human tissue, i.e., they exhibit exceptionally low ocular irritation and oral toxicity, and are, therefore, eminently suited and useful as surface active agents in personal care compositions, such as shampoos, conditioners and the like.

In the preparation of the various phosphate substituted compounds set forth above, the processes generally comprise two steps: (1) reaction of an inorganic phosphate salt with epihalohydrin to yield a phosphate ester alkylating agent and (2) reaction of a substituted amine with the phosphate ester alkylating agent to form the desired phosphate substituted compound.

In U.S. Pat. No. 4,283,542 which describes processes for the preparation of phosphobetaines, there is a general description of the above process. In column 11 of that patent, a process is described comprising the reaction of epichlorohydrin with phosphoric acid and various phosphate salts. The most important reaction parameter is said to be the pH of the phosphate salt. It is said that the pH must be strictly controlled and "The desired pH range is from 4 to 5. If the pH drops below 4, there is significant hydrolysis of the phosphate ester. If the pH at which the reaction is run is too high, there will be a loss of labile organic chlorine. When the reaction is carried out in an alkaline environment of a pH 9.5–10.5 optionally, the resulting intermediate had surprisingly lost its labile organic chlorine and formed a cyclic diester . . . The phosphate salt used should have the pH of 9.5–10.5 before the addition of epichlorohydrin. This will allow for maximum formation of the cyclic phosphate diester." The yields are relatively low for this described process.

SUMMARY OF THE INVENTION

It is an object of this invention to provide an improved process for the preparation of phosphate surfactants.

It is another object of this invention to provide a process for the preparation of phosphate surfactants with improved yields of said phosphate surfactants.

Other objects of this invention will be set forth in, or be apparent from, the following detailed description of the invention.

The foregoing objects and other features and advantages of the present invention are achieved by a process comprising the steps of reacting (1) an inorganic phosphate salt with epihalohydrin and (2) reacting the resulting phosphate ester alkylating agent with a substituted amine to form the desired phosphate substituted compound wherein the first reaction is carried out within a specific pH range.

DETAILED DESCRIPTION OF THE INVENTION

The foregoing objects are obtained in a process comprising the steps of
(1) reacting an inorganic phosphate salt with epichlorohydrin to obtain a phosphate ester alkylating agent; and
(2) reacting said phosphate ester alkylating agent with a substituted amine to obtain the desired phosphate substituted compound
wherein step (1) of the process is carried out at a pH of from about 5.4 to 7.0.

It has been found, notwithstanding the disclosures in the prior art, that if the pH is lower than about 5.4, the yield of the desired ester will be low, whereas if the pH is greater than about 7.0, the phosphate ester yield will be higher, but the amount of released chloride will also be greater resulting in additional process separation or higher contamination of the desired alkylating agent with inactive by-products thereby resulting in a lower final yield and therefore a more costly process.

The inorganic phosphate salts which are useful in the present invention are appropriate mixtures of the following which are made to achieve the desired pH range, or acidic reagents may be adjusted to the desired pH level with NaOH. However, alkaline reagents may not be adjusted to the appropriate pH with external acids, for example, $Na_3PO_4$ must be adjusted to the appropriate pH with $H_3PO_4$, not with another acid such as HCl or $H_2SO_4$.

If the desired end-product is a phosphobetaine compound, the suitable phosphate compounds are: $H_3PO_4$, $NaH_2PO_4$, $Na_2HPO_4$, $Na_3PO_4$ and related compounds.

If the desired end-product is a pyrophosphobetaine compound, the suitable phosphate compounds are: $H_4P_2O_7$, $Na_2H_2P_2O_7$, $Na_4P_2O_7$ and related compounds.

If the desired end-product is a phosphite compound, the suitable phosphate compounds are: $H_3PO_3$, $Na_2HPO_3$ and related compounds.

These inorganic phosphate salts are reacted with epihalohydrin of the formula

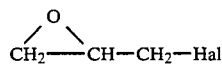

to form the phosphate ester alkylating agent. The preferred epihalohydrin is epichlorohydrin of the formula

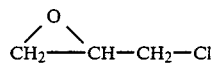

Once again, as stated above, it is essential in the process of the present invention that the pH be within the range of from about 5.4 to 7.0 in order to achieve the desired results of good yield and favorable economic conditions. It has been found that if this step of the process is carried out at the pH ranges taught in the prior art, the yields will be much lower and significant amounts of side products are formed making the yield of the desired surfactant lower and, due to by-product contamination, surfactant performance may be unsatisfactory.

Epihalohydrin, preferably epichlorohydrin, is desirable as a linking agent since it has two reactive functions, expoxide and alkyl halide, with different reactivities such that one or the other may be selected by virtue of the reaction conditions. Thus, in the present invention, inorganic phosphate reagents may be linked to the alkyl halide function by the reaction of the phosphate with the expoxide at an acid pH. The alkyl halide function may then be used in a reaction with a suitable amine to form the desired surfactant containing phosphate anionic groups and ammonium cationic group. If the reaction is unsuccessful at either stage, that is, at the phosphate-epoxide reaction or at the alkyl halide-amine reaction, the desired surfactant is not formed. At low pH, i.e. less than about pH 5.4, the reaction of phosphate with epoxide fails, and instead hydrolysis of the epihalohydrin to dihydroxypropyl halide predominates. If this product is reacted with the amine, the alkyl halide reacts to form a surfactant having only the ammonium cationic group, that is a dihydroxypropyl substituted cationic.

At high pH, i.e. greater than about 7, the reaction of phosphate with epihalohydrin occurs, but with cleavage of the alkyl halide to form an inorganic chloride. Thus no group reactive to amine remains, and so the amine remains unchanged.

Only in the specific pH range of the present invention is the phosphate linkage to epihalohydrin occurring in high yield with little hydrolysis of chloride. This intermediate then has the optimal utility in the formation of the desired phosphate surfactant when reacted with the amine.

The phosphate ester alkylating agents formed by the reaction of the phosphate salt and epihalohydrin are of the following formuli, respectively,

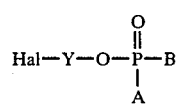

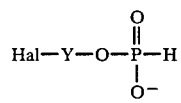

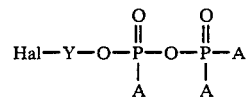

The appropriate phosphate ester alkylating agent is then reacted with a substituted amine to form the desired phosphate substituted compound.

The amines which are useful are primary, secondary and tertiary amines of the following formuli:

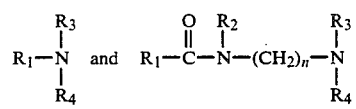

wherein $R_1$, $R_2$, $R_3$ and $R_4$ are as defined below.

The resultant phosphate substituted compounds are of the general formula

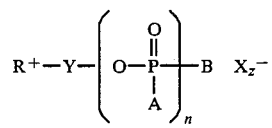

wherein

A is selected from $O^-$, OM and $O-Y-R^+$

B is selected from $O^-$, OM and H

X is an anion n is an integer of 1 or 2

Z is an integer from 0 to 3 as required for charge balance.

R is an amine or an amidoamine moiety of the formula

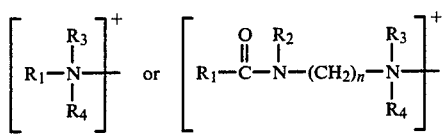

wherein $R_1$ is an alkyl, alkenyl, alkoxy, or hydroxyalkyl of from 5 to 22 carbon atoms, each, or aryl or alkaryl of up to 20 carbon atoms, $R_2$ is hydrogen or alkyl, hydroxyalkyl or alkenyl of up to 6 carbon atoms each or cycloalkyl of up to 6 carbon atoms, or polyoxyalkalene of up to 10 carbon atoms, $R_3$ and $R_4$, which may be the same or different, are selected from alkyl, hydroxyalkyl, carboxyalkyl of up to 6 carbon atoms in each alkyl moiety, and polyoxyalkylene of up to 10 carbon atoms; in addition, $R_3$ and $R_4$ taken together with the nitrogen to which they are attached, may represent an N-heterocycle, e.g., a moropholino structure, in which the Y radical is bonded to a ring atom of said N-heterocycle other than the nitrogen of the R moiety;

n is an integer from 2 to 12;

Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each;

M is hydrogen, an organic radical selected from alkyl or hydroxyalkyl of up to 6 carbon atoms, polyhydroxyalkyl of up to 10 carbon atoms, glceryl, cycloalkyl of up to 6 carbon atoms, aryl or arylalkyl of up to 10 carbon atoms, or a salt radical selected from alkali metals (e.g., sodium, potassium, or ammonium and substituted ammonium radicals) and alkaline earth metals (e.g., magnesium or calcium).

The term "polyoxyalkalene" as used above in the definition of $R_2$, $R_3$ and $R_4$ may be of the formula $(R_5-O-R_5')m$, wherein $R_5$ and $R_5'$ are alkyl of from 1 to 4 carbon atoms and m is an integer from about 2 to 10.

The following examples will illustrate in detail the manner in which the present invention may be practiced. It will be understood, however, that the invention is not confined to the specific limitations set forth in the individual examples, but rather to the scope of the appended claims.

EXAMPLE I

In a suitable reactor equipped with condenser, stirring and controlled heating equipment are combined sodium dihydrogen phosphate (138 g as the monohydrate, 1.0 mole), disodium hydrogen phosphate (268 g as the heptahydrate, 1.0 mole) and water (1000 g).

After dissolution (pH 6.3) and warming to 80° C., epichlorohydrin (185 g, 2.0 mole) is added and the mixture is stirred at 80° C. for one hour. The reduction of phosphate titer is equivalent to consumption of 1.5 mole of phosphate (75%) and inorganic chloride titer is equivalent to 0.24 mole (12%).

EXAMPLE II

In a suitable reactor equipped for stirring and heating are combined water (300 ml) and the phosphate-epichlorohydrin reaction product of Example I, (117 g). The solution is adjusted to pH 8 with 50% sodium hydroxide and lauramidopropyldimethylamine (45.4 g) is added. The mixture is heated to 85° C. and stirred at that temperature for 2 hours, until all organic chlorine and amine starting material are consumed. The product is analyzed and found to be a phosphobetaine surfactant as described in U.S. Pat. No. 4,215,064.

EXAMPLE III

In a suitable reactor are combined tetrasodium pyrophosphate (159.6 g, 0.6 mole), sodium acid pyrophosphate (266.4 g, 1.2 moles) and water (1400 ml). The mixture (pH 5.7) is heated to 75° and epichlorohydrin (166.5 g, 1.8 moles) is added to the stirred solution. After 1½ hours, the reaction is complete, with 68% reduction of inorganic pyrophosphate and 7% release of inorganic chloride.

EXAMPLE IV

In a suitable reactor are combined the epichlorohydrin-pyrophosphate reaction product of Example III (400 g), lauramidopropyldimethylamine (71 g) and 50% sodium hydroxide (50 ml). The mixture is stirred at 85° C. for two hours. The product is a pyrophosphobetaine surfactant as described in U.S. Pat. No. 4,382,036.

EXAMPLE V

In a suitable reactor are combined phosphorous acid (41 g), water (409 g) and 50% NaOH (50 g) and the solution (pH 6) is warmed to 75° C. Epichlorohydrin (46.25 g) is added and the mixture stirred at 75° C. for 1½ hours.

Phosphite is reduced by 64% and chloride release is 7%.

EXAMPLE VI

In a suitable reactor are combined the epichlorohydrin-phosphite reaction product of Example V (546.25 g), 50% sodium hydroxide to achieve pH 8, and lauramidopropyldimethylamine (88 g).

The mixture is stirred at 80° C. for 2 hours. The product is a phosphite surfactant as described in U.S. Pat. No. 4,261,911.

In order to demonstrate the pH-dependent nature of the reaction of the inorganic phosphate salt with epihalohydrin, the following tests are carried out.

EXAMPLE VII

Solution A was prepared with sodium dihydrogen phosphate (138 g as the monohydrate, 1 mole) made to 1000 g with distilled water. Solution B was prepared with disodium hydrogen phosphate (268 g as the heptahydrate, 1 mole) made to 1000 g with distilled water. Various weight ratios totaling 100 g. (0.10 mole of phosphate) of solutions A and B were made; the pH measured, and then they were reacted with epichlorohydrin (9.25 g, 0.10 mole) in a suitable reactor equipped with condenser, stirring and controlled heating apparatus at 75° C. for 90 minutes. The reactions were assayed for the amount of phosphate ester formation and the amount of chloride hydrolysis.

The results are tabulated in Table I below and plotted in FIG. I.

| Solution A (ml) | Solution B (ml) | pH | % phosphate ester formation | % chloride formation |
|---|---|---|---|---|
| 100 | 0 | 4.3 | 24.7 | 0.5 |
| 95 | 5 | 4.9 | 37.0 | — |

-continued

| Solution A (ml) | Solution B (ml) | pH | % phosphate ester formation | % chloride formation |
| --- | --- | --- | --- | --- |
| 90 | 10 | 5.3 | 42.0 | 0.5 |
| 85 | 15 | 5.6 | 45.6 | — |
| 80 | 20 | 5.8 | 49.3 | 1.1 |
| 70 | 30 | 6.1 | 64.5 | 4.1 |
| 50 | 40 | 6.35 | 68.9 | 6.1 |
| 60 | 50 | 6.6 | 78.9 | 12.0 |
| 40 | 60 | 6.85 | 82.6 | 14.5 |

EXAMPLE VIII

Solution C was prepared with sodium acid pyrophosphate ($Na_2H_2P_2O_7$, .222 g, 1.0 mole) made to 1000 g with distilled water. Solution D was prepared with tetrasodium pyrophosphate (133 g, 0.5 mole) and sodium acid pyrophosphate (111 g, 0.5 mole) made to 1000 g with distilled water.

Various weight ratios totaling 100 g (0.10 mole of pyrophosphate) of solutions C and D were made, the pH measured, and then reacted with epichlorohydrin (9.25 g, 0.10 mole) in a suitable reactor as described in Example VII.

The reactions were assayed for amount of pyrophosphate ester formation and amount of inorganic chloride formation and the results are tabulated in Table II below and plotted in FIG. II.

| Solution C (ml) | Solution D (ml) | pH | % pyrophosphate ester formation | % chloride formation |
| --- | --- | --- | --- | --- |
| 100 | 0 | 4.19 | 17.8 | 0.4 |
| 80 | 20 | 5.24 | 30.2 | 0.4 |
| 50 | 50 | 5.80 | 39.6 | 2.2 |
| 20 | 80 | 6.34 | 49.4 | 5.2 |
| 0 | 100 | 6.81 | 61.6 | 11.8 |

EXAMPLE IX

A series of solutions of phosphorous acid (8.2 g, 0.1 mole) in water were made to varying pH levels by the addition of 50% sodium hydroxide such that the final solution weight is 100 g. Each solution was reacted with epichlorohydrin (9.25 g, 0.1 mole) in a suitable reactor as described in Example VII. The reactions were assayed for amount of phosphite ester formation and amount of inorganic chloride formation and the results tabulated in Table III below and plotted in FIG. III.

TABLE III

| Solution composition | | pH | % phosphite ester formation | % chloride formation |
| --- | --- | --- | --- | --- |
| $H_3PO_3$ | 50% NaOH | | | |
| 8.2 | 8.0 | 3.79 | 20.9 | 1.1 |
| 8.2 | 9.0 | 5.37 | 49.1 | 1.1 |
| 8.2 | 10.0 | 5.80 | 63.6 | 7.1 |
| 8.2 | 11.0 | 6.05 | 72.7 | 17.5 |
| 8.2 | 12.0 | 6.29 | 83.6 | 34.4 |
| 8.2 | 13.0 | 6.56 | 87.7 | 51.3 |

The results in Examples VII, VIII and IX demonstrate the importance of the specific pH range of the process of the present invention.

What is claimed is:

1. In a process for the preparation of phosphate compounds of the formula

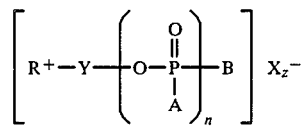

comprising the steps of
(1) reacting an inorganic phosphate salt with epichlorohydrin to obtain a phosphate ester of the formula

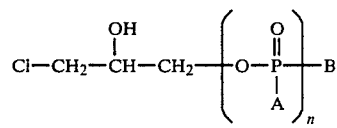

(2) reacting the phosphate ester with a substituted amine selected from the group consisting of

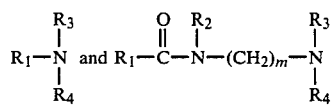

wherein
A is selected from O—, OM and O—Y—K+;
B is selected from O—, OM and H;
X is an anion;
n is an integer of 1 or 2;
z is an integer from 0 to 3 as required for charge balance;
m is an integer of from 2 to 12;
Y is alkylene or substituted alkylene;
M is hydrogen, an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or a salt radical;
R is an amine or an amidoamine moiety of the formula

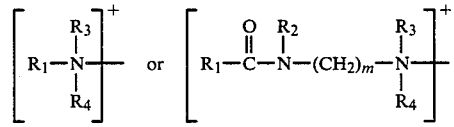

$R_1$ is an alkyl, alkenyl, alkoxy, or hydroxyalkyl of from 5 to 22 carbon atoms each, or aryl or alkaryl of up to 20 carbon atoms;
$R_2$ is hydrogen or alkyl, hydroxyalkyl or alkenyl of up to 6 carbon atoms each or cycloalkyl of up to 6 carbon atoms, or polyoxyalkylene of up to 10 carbon atoms;
$R_3$ and $R_4$ are the same or different and are selected from alkyl, hydroxyalkyl, carboxyalkyl of up to 6 carbon atoms in each alkyl moiety, and polyoxyalkylene of up to 10 carbon atoms; and in addition, $R_3$ and $R_4$ taken together with the nitrogen to which they are attached, may represent an N-heterocycle, in which the Y radical is bonded to a ring atom of said N-heterocycle other than the nitrogen of the R moiety;

and wherein the improvement comprises carrying out step (1) of the process at a pH of from about 5.4 to 7.0.

2. The process of claim 1 wherein the resulting phosphate compound is a phosphobetaine of the formula

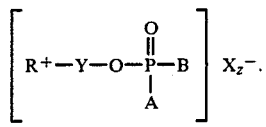

3. The process of claim 1 wherein the resulting phosphate compound is a phosphitaine of the formula

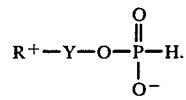

4. The process of claim 1 wherein the resulting phosphate compound is a pyrophosphobetaine of the formula

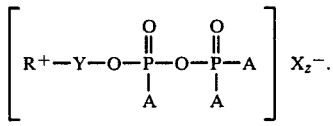

* * * * *